United States Patent [19]

Wallroth et al.

[11] Patent Number: 5,062,999
[45] Date of Patent: Nov. 5, 1991

[54] VAPORIZER FOR AN ANESTHETIC MEDIUM

[75] Inventors: Carl F. Wallroth, Lübeck; Wolfgang Falb, Krummesse; Helmut Mohr, Stockelsdorf, all of Fed. Rep. of Germany

[73] Assignee: Drägerwerk Aktiengesellschaft, Lübeck, Fed. Rep. of Germany

[21] Appl. No.: 507,953

[22] Filed: Apr. 12, 1990

[30] Foreign Application Priority Data

Apr. 19, 1989 [DE] Fed. Rep. of Germany ....... 3912818

[51] Int. Cl.⁵ .................. B01F 3/04; A61M 11/04
[52] U.S. Cl. .................... 261/39.1; 261/63; 261/DIG. 65; 128/203.14; 128/204.14
[58] Field of Search ............ 128/203.14, 204.14, 128/203.17, 203.26, 203.27, 204.17; 261/39.1, 63, DIG. 65

[56] References Cited

U.S. PATENT DOCUMENTS

| | | | |
|---|---|---|---|
| 3,534,732 | 10/1970 | Bickford | 128/203.14 |
| 3,588,057 | 6/1971 | Breiling | 261/39.1 |
| 3,630,438 | 12/1971 | Bickford | 251/205 |
| 3,671,024 | 6/1972 | Breiling | 128/203.14 |
| 3,833,171 | 9/1974 | Gifford | 261/39.1 |
| 4,017,566 | 4/1977 | Seidel | 261/39.1 |
| 4,059,657 | 11/1977 | Hay | 261/39.1 |
| 4,879,997 | 11/1989 | Bickford | 128/203.26 |

FOREIGN PATENT DOCUMENTS 648191 1/1951 United Kingdom ........... 128/203.14

Primary Examiner—Tim Miles
Attorney, Agent, or Firm—Walter Ottesen

[57] ABSTRACT

The invention is directed to a vaporizer for an anesthetic medium having a throttle arrangement for throttling the gas flowing therethrough. A compensating arrangement is provided for adjusting a throttle gap in dependence upon ambient temperature and has a rod body made of a material having a low thermal coefficient of expansion. This rod body is accommodated in a sleeve made of a material having a high thermal coefficient of expansion. The rod body is tightly joined at one end thereof to the sleeve and, at its other end, the rod body is joined to a molded part. This molded part and a second molded part conjointly define the throttle gap. With the invention, a thermal adjustment device is provided for the throttle gap for which only simply formed parts are used and which are made of material not resistant to corrosion and which are easily galvanized. The housing of the throttling device is of a complicated configuration and can be made of a corrosion resistant material. The sleeve is surrounded by an enclosure made of corrosion resistant material which is closed in a gastight manner with respect to the throughflow channel conducting the anesthetic gas. The sleeve rests on its sleeve support at its end facing toward the molded part.

7 Claims, 1 Drawing Sheet

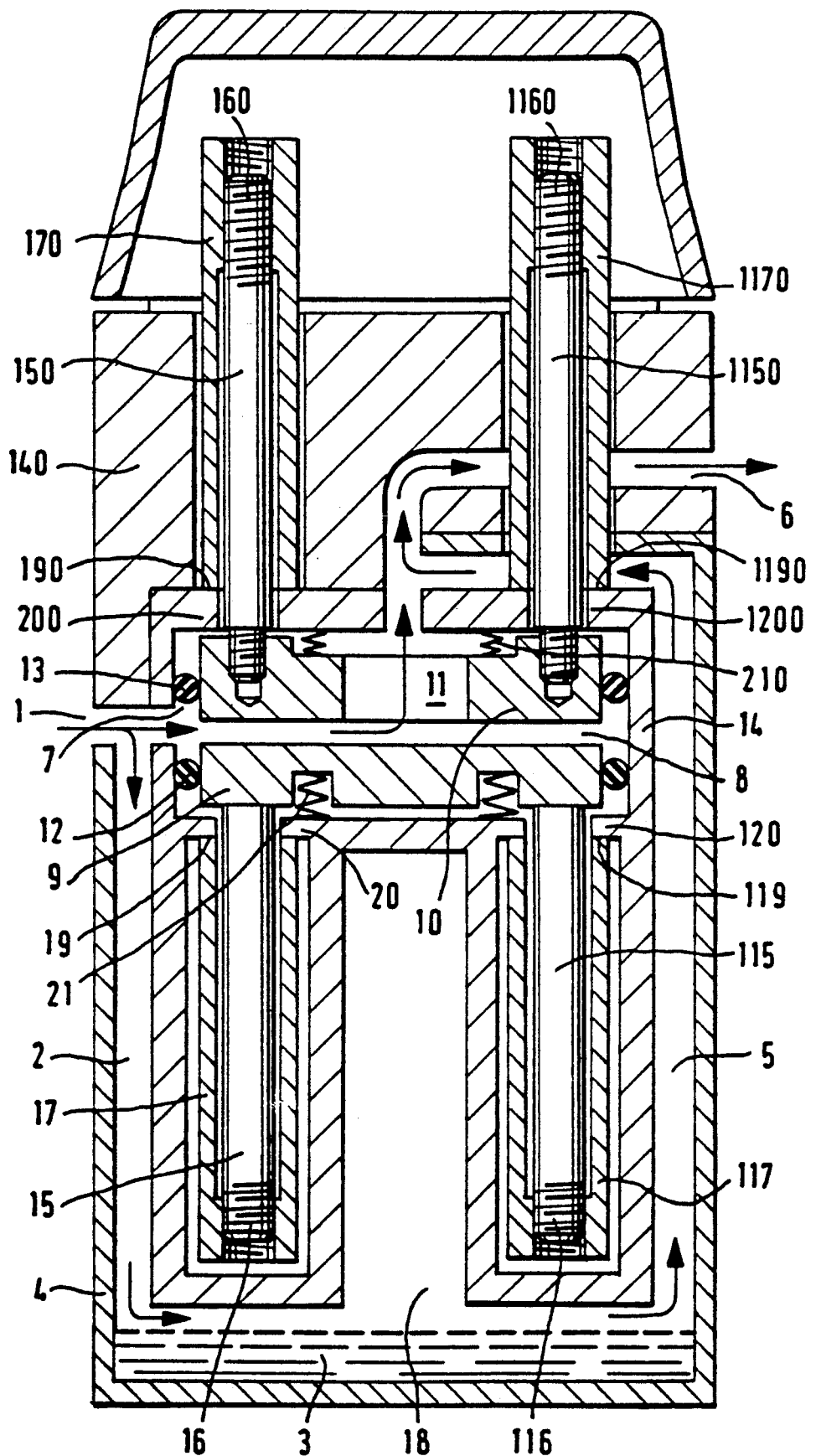

VAPORIZER FOR AN ANESTHETIC MEDIUM

FIELD OF THE INVENTION

The invention relates to a vaporizer for an anesthetic medium wherein the gas flowing therethrough is throttled. The vaporizer includes a throttle gap which is adjustable by means of a compensating device in dependence upon the ambient temperature. The compensating device includes a part having rods and being made of a material having a low thermal coefficient of expansion and this part is accommodated in a sleeve made of a material having a high thermal coefficient of expansion. At its one end, the rod body is firmly connected with the sleeve and, at its other end, the rod body is connected with a molded part. This molded part and a second molded part conjointly define the throttle gap.

BACKGROUND OF THE INVENTION

A vaporizer for an anesthetic medium is disclosed in U.S. Pat. No. 4,017,566. This vaporizer includes a bypass connected in parallel to the vaporizing chamber. To maintain the quantity of the vaporized anesthetic medium so as to be as independent as possible from the temperature of the apparatus, the gas quantity flowing through the bypass is controlled by changing a throttle gap in dependence upon the temperature of the apparatus. In this vaporizer, the high thermal expansion of the interconnected housing parts of the vaporizing chamber and of the adjusting device connected to the vaporizing chamber are utilized to control the width of the throttle gap. A temperature-dependent throttle-gap width is obtained by connecting components having a low thermal coefficient of expansion. The housing parts are made of brass and have a very complicated configuration with narrow inner contours.

Since anesthetic media are very corrosive, the housing must be protected against corrosion by providing a nickel coating for example. However, this is at best unsatisfactory because of the complicated geometry of the assembly parts conducting the anesthetic gas. The component parts defining the throttle gap are provided with layers of different thicknesses because of the nickel plating which layers are measured with respect to the required tight tolerances. Since these layers are not adequately uniform, a dosage having the required accuracy can only be assured with difficulty.

SUMMARY OF THE INVENTION

It is an object of the invention to provide a vaporizer having a thermal adjusting device for adjusting the throttle gap with which only parts having a simple configuration can be used. It is a further object of the invention to provide such a vaporizer wherein the material of these parts can be selected with respect to a favorable thermal coefficient of expansion without having to consider resistance to corrosion.

The vaporizer of the invention is for adding an anesthetic medium to a gas. The vaporizer includes: a housing defining a reservoir for holding the anesthetic medium; the housing having inlet means for receiving the gas and outlet means for conducting the gas out of the vaporizer; passage means extending from the inlet for passing a first component of the gas over the anesthetic medium so as to cause the first component to entrain vapors of the anesthetic medium therein; first and second members mounted in the housing to conjointly define throttling gap means for throttling a second component of the gas entering the inlet means and passing the throttled second component to the outlet means to mix with the first component; temperature-responsive compensation means connected to one of the members for displacing the one member in dependence upon ambient temperature so as to adjust the width of the gap means thereby increasing or decreasing the quantity of the gas of the second component; and, an enclosure made of corrosion-resistant material disposed in the housing so as to enclose the compensation means in a gastight manner with respect to the passage means.

The advantage of the invention is seen essentially in that only the simply formed enclosure comes in contact with the corrosive gas to be metered such as an anesthetic medium. This enclosure can be easily made resistant to corrosion, for example, with nickel plating or the enclosure itself can be made of a corrosion-resistant material. The molded parts defining the throttle gap are no longer responsible for adapting the gap width to a changed temperature so that the material thereof likewise must only be selected with reference to a good resistance to corrosion and so that they can be produced to have a precise fit. The rods and the sleeve support are connected with each other only at the end of the rods facing away from the molded part and by means of the floating support of the rods, a good utilization of the linear expansion relative to precisely changeable gap widths is achieved.

A nickel-iron alloy (Invar) is preferably used as a material having a low thermal coefficient of expansion. Brass is preferably used as a material having a high thermal coefficient of expansion.

The sensitivity of the thermal control of the throttle gap can be achieved by extending the lengths of the rods and sleeves. On the other hand, it is also possible to arrive at this objective in that the upper ring is configured to provide an equivalent thermal adjustment and can also be made of rods connected to the sleeves.

BRIEF DESCRIPTION OF THE DRAWING

The invention will now be described with reference to the drawing having a single figure showing an elevation view, in section, of the vaporizer according to the invention. The vaporizer of the invention includes an arrangement for throttling the flow of gas to be metered.

DESCRIPTION OF THE PREFERRED EMBODIMENTS OF THE INVENTION

The gas to be metered flows through the inlet 1 and divides into two component flows. The first component flow flows downwardly through the channel 2 to the anesthetic medium 3 disposed in the anesthetic container 4. The first component flow passes over the surface of the anesthetic medium and becomes saturated with anesthetic. The saturated gas then rises through the channel 5 and leaves the vaporizer through the outlet 6.

The second component flow of the gas flowing in through the inlet 1 reaches the annular chamber 7. The gap 8 is defined by the respective end faces of a first molded part 9 and an annularly-shaped second molded part 10. The gap 8 influences the quantity of gas which flows into the chamber 11 and onto the outlet 6 in that it becomes mixed with the first component flow saturated with anesthetic. The molded parts (9 and 10) are sealed with respect to the enclosure 14 via O-ring seals (12 and 13). The first molded part 9 is formed as a yoke and connected to rods (15, 115) made of Invar and is held with respect to the sleeve support (20, 120) via the resilient elements 21. The rods (15, 115) are threadably engaged at their attachment ends (16, 116) with respective sleeves (17, 117) made of brass and are supported at their other ends (19, 119) on a sleeve support (20, 120) of the enclosure 14.

When heated, the brass sleeves (17, 117) expand in their length substantially more than the Invar rods (15, 115) and the enclosure 14 made of a rust-proof steel. As a consequence of the foregoing, the throttle gap 8 widens and the quantity of gas flowing therethrough increases. In this way, the increased vaporization of the anesthetic 3 because of a temperature increase is counteracted in the vaporization chamber 18 of the anesthetic vaporizer. The mixture formed from the gas quantities which have flowed through the vaporization chamber and through the throttle gap 8 have a content of anesthetic which is approximately independent of temperature.

The second molded part 10 is provided with an adjustment device in order to increase the thermally-conditioned gap width variation. This adjustment device is equivalent to the adjusting device of molded part 9.

The second molded part 10 is configured as a yoke and connected to rods (150, 1150) made of Invar and is held with respect to the sleeve support (200, 1200) via resilient elements 210. The rods (150, 1150) are threadably connected to brass sleeves (170, 1170) at their respective attachment ends (160, 1160). The brass sleeves (170, 1170) expand or contract in dependence upon ambient temperature and, when heated, the brass sleeves (170, 1170) expand in their length substantially more than the Invar rods (150, 1150). The rods are supported via the sleeves at the ends (190, 1190) on a sleeve support (200, 1200) of the adjustment part 140.

It is understood that the foregoing description is that of the preferred embodiments of the invention and that various changes and modifications may be made thereto without departing from the spirit and scope of the invention as defined in the appended claims.

What is claimed is:

1. A vaporizer for adding an anesthetic medium to a gas comprising:
   a housing defining a reservoir for holding the anesthetic medium;
   said housing having inlet means for receiving the gas and outlet means for conducting the gas out of the vaporizer;
   passage means extending from said inlet for passing a first component of the gas over said anesthetic medium so as to cause said first component to entrain vapors of the anesthetic medium therein;
   first and second members mounted in said housing to conjointly define throttling gap means for throttling a second component of the gas entering said inlet means and passing the throttled second component to said outlet means to mix with said first component;
   first temperature-responsive compensation means connected to one of said members for displacing said one member in dependence upon ambient temperature so as to adjust the width of said gap means thereby increasing or decreasing the quantity of the gas of said second component;
   second temperature-responsive means connected to the other one of said members for displacing said other one of said members in dependence upon ambient temperature to coact with said first temperature-responsive means for adjusting the width of said gap means; and,
   an enclosure made of corrosion-resistant material disposed in said housing so as to enclose said compensation means in a gastight manner with respect to said passage means.

2. The vaporizer of claim 1, said first compensation means including:
   a rod-like body having two ends and one of said ends being connected to said one member;
   a sleeve-like body for accommodating said rod-like body therein and having a first end connected to the other end of said rod-like body;
   said sleeve-like body having a second end facing toward said one member;
   seat means formed on said enclosure for receiving said second end thereby supporting said sleeve-like body thereon;
   said rod-like body being made of a material having a first thermal coefficient of expansion and said sleeve-like body being made of a material having a second thermal coefficient of expansion; and,
   one of said coefficients of expansion being greater than the other one of said coefficients of expansion.

3. The vaporizer of claim 2, said first coefficient being less than said second coefficient.

4. The vaporizer of claim 3, said material of said rod-like body being a nickel-iron alloy.

5. The vaporizer of claim 4, said material of said sleeve-like body being brass.

6. A vaporizer for adding an anesthetic medium to a gas comprising:
   a housing defining a reservoir for holding the anesthetic medium;
   said housing having inlet means for receiving the gas and outlet means for conducting the gas out of the vaporizer;
   passage means extending from said inlet means for passing a first component of the gas over said anesthetic medium so as to cause said first component to entrain vapors of the anesthetic medium therein;
   first and second members mounted in said housing to conjointly define throttling gap means for throttling a second component of the gas entering said inlet means and passing the throttled second component to said outlet means to mix with said first component;
   temperature-responsive compensation means connected to one of said members for displacing said one member in dependence upon ambient temperature so as to adjust the width of said gap means thereby increasing or decreasing the quantity of the gas of said second component;
   an enclosure made of corrosion-resistant material disposed in said housing so as to enclose said compensation means in a gastight manner with respect to said passage means; and,
   said compensation means including: two rod-like bodies; each of said rod-like bodies having two ends and one of said ends being connected to said one member so as to cause said member and said rod-like bodies to conjointly define a U-shaped unit; two sleeve-like bodies for accommodating respective ones of said rod-like bodies therein; each of said sleeve-like bodies having a first end connected to the other end of said rod-like body accommodated therein; each of said sleeve-like bodies having a second end facing toward said one member; first and second seat means formed on said enclosure for receiving the second ends of corresponding ones of said sleeve-like bodies thereby supporting said sleeve-like bodies thereon; and, each of said rod-like bodies being made of a material having a first thermal coefficient of expansion and each of said sleeve-like bodies being made of a material having a second thermal coefficient of expansion and one of said coefficients of expansion being greater than the other one of said coefficients of expansion.

7. The vaporizer of claim 6, said first coefficient being less than said second coefficient.

* * * * *